United States Patent [19]

Lesniak

[11] Patent Number: 5,201,582
[45] Date of Patent: Apr. 13, 1993

[54] DIFFERENTIAL TEMPERATURE STRESS MEASUREMENT EMPLOYING ARRAY SENSOR WITH LOCAL OFFSET

[75] Inventor: Jon R. Lesniak, Madison, Wis.

[73] Assignee: Stress Photonics, Inc., Madison, Wis.

[21] Appl. No.: 884,067

[22] Filed: May 15, 1992

[51] Int. Cl.$^5$ .................. G01N 25/00; G01N 3/32
[52] U.S. Cl. ............................ 374/45; 374/120;
250/370.03; 250/332; 358/113; 73/808
[58] Field of Search ............ 250/370.08, 370.13,
250/332; 73/788, 808; 358/106, 113, 337;
374/4, 5, 45, 46, 47, 120

[56] References Cited

U.S. PATENT DOCUMENTS

| | | | |
|---|---|---|---|
| 3,934,452 | 1/1976 | Prevorsek et al. | 73/15.6 |
| 4,126,033 | 11/1978 | Bartoli et al. | 374/5 |
| 4,378,701 | 4/1983 | Mountain et al. | 73/808 |
| 4,541,059 | 9/1985 | Toshihiko | 364/508 |
| 4,607,963 | 8/1986 | Ulrickson | 374/131 |
| 4,625,545 | 12/1986 | Holm et al. | 374/4 |
| 4,798,477 | 1/1989 | Mountain | 374/45 |
| 4,828,400 | 5/1989 | Boyce | 374/46 |
| 4,868,389 | 9/1989 | Moore | 250/332 |
| 4,878,116 | 10/1989 | Thomas et al. | 358/160 |
| 4,955,236 | 9/1990 | Yokoyama et al. | 73/655 |
| 4,969,037 | 11/1990 | Poleschinski et al. | 358/113 |

OTHER PUBLICATIONS

"128×128 InSb InfraRed Imaging System," Amber Engineering, Inc., Santa Barbara, Calif.
"Spate 9000 Dynamic Stress Analyzer," Ometron Limited, London, England.

Primary Examiner—William A. Cuchlinski, Jr.
Assistant Examiner—G. Bradley Bennett
Attorney, Agent, or Firm—Lathrop & Clark

[57] ABSTRACT

The instrument has a focal plane array of infrared sensors of the integrating type such as a multiplexed device in which a charge is built up on a capacitor which is proportional to the total number of photons which that sensor is exposed to between read-out cycles.

The infrared sensors of the array are manufactured as part of an overall array which is part of a micro-electronic device. The sensor achieves greater sensitivity by applying a local offset to the output of each sensor before it is converted into a digital word. The offset which is applied to each sensor will typically be the sensor's average value so that the digital signal which is periodically read from each sensor of the array corresponds to the portion of the signal which is varying in time. With proper synchronization between the cyclical loading of the test object and the frame rate of the infrared array the output of the A/D converted signal will correspond to the stress field induced temperature variations. A digital lock-in operation may be performed on the output of each sensor in the array. This results in a test instrument which can rapidly form a precise image of the thermoelastic stresses in an object.

29 Claims, 3 Drawing Sheets

DIFFERENTIAL TEMPERATURE STRESS MEASUREMENT EMPLOYING ARRAY SENSOR WITH LOCAL OFFSET

LICENSE RIGHTS

The U. S. Government has a paid-up license in this invention and the right in limited circumstances to require the patent owner to license others on reasonable terms as provided for by the terms of contract #NAS1-19262 awarded by NASA.

FIELD OF THE INVENTION

This invention relates to methods and apparatus for making differential thermal measurements of an object over an extended area in general and to apparatus and methods employing an infrared focal plane array in particular.

BACKGROUND OF THE INVENTION

In the design of new structures and the testing of existing structures it is desirable to know the distribution of stresses within the structure.

In the design of new structures weight and cost of the structure may be minimized by designing the structure so that the stresses are uniformly distributed throughout the structure. Stress concentrations caused by faulty design often lead to failure of the structure or to a shortened useful life. In an existing structure such as an airplane or steel bridge, the stresses can often indicate incipient and hidden flaws or cracks in the structure which may lead to eventual failure. One method which has been developed for determining the distribution of stresses within a structure involves employing the thermoelastic effect.

When a given volume of gas is compressed, its temperature increases. When the gas is expanded, its temperature decreases. In a similar way, solids which are under compression or tension undergo minute changes in volume which result in small but measurable changes in temperature. Systems employing the thermoelastic principle to determine the distribution of stresses in a structure employ infrared (I.R.) cameras to detect the patterns of stress on the structures. However, the temperature change caused by applying stress to a material is very small. At room temperature the application of a stress of about 150 psi causes about 0.001 degree Kelvin temperature change in steel. A typical D.C. or steady state infrared camera is unable to see temperature changes of this magnitude. Because of the statistical nature of the way infrared radiation or the photon flux is emitted from a surface the I.R. detectors used in infrared cameras are quite noisy and hide the temperature change caused by the applied stress. When the loads are applied periodically the temperature changes corresponding to the stresses in the material become periodic in nature. Given that the temperature changes which relate to the stress in the test object are periodic it is then possible to use various signal processing techniques to reduce the signal noise and detect the stress-related temperature changes.

One type of known camera is an analog slow scan camera. This is a raster scanning signal detector camera which completely processes the I.R. signal for each scanned point on an object before moving on to the next point. It utilizes a lock-in amplifier and averaging of the sampled lock-in output to reduce signal noise. Likewise, digital slow scan cameras are known where the output of the I.R. detector is digitally sampled. Signal extraction is performed with a digital lock-in operation, and noise is further rejected by the use of a band limiting low pass filter. The slow scan cameras can achieve temperature sensitivities of 0.001 degrees K but generally require long periods of time on the order of an hour or more for a single temperature profile over a scanned object.

Another known system is the video fast scan camera. This system is based on a single detector and a fast scan mirror set, and provides its output in video format. Every point in the scan is sampled at the video frame rate, typically at 30 times per second. This results in a very short sample time for each point on the object which results in a noisy signal.

The video fast scan camera rapidly scans the object but, because of the noise problems associated with the short sample time, many scans are required to detect the temperature profile of the specimen. Hence, the overall time for obtaining a stress profile thermal image is not appreciably enhanced over a slow scan camera. The nature of the video frame rate requires that the specimen be loaded in exact synchronization with the frame rate. This synchronization requirement makes video scan systems difficult to employ. Array fast scan cameras are known which can rapidly produce a thermal image of a specimen. However these array cameras are not designed or optimized to detect the very small temperature changes produced by the stress profiles within the object.

Due to the slow speed of the thermoelastic effect imaging systems hithertofore available, the application of the thermoelastic technique for determining stresses in materials has been limited to applications where the time and expense of employing existing equipment could be justified.

What is needed is a thermoelastic detection system which can rapidly image an object and so cost effectively determine the stresses therein.

SUMMARY OF THE INVENTION

The stress measurement instrument of the present invention employs a focal plane array of infrared detectors. The array is mounted in a dewar containing liquid nitrogen which cools the array to reduce thermal noise. An infrared optical train including an infrared optical window in the dewar projects an infrared image of an object undergoing cyclical stress onto the focal plane array. The sensors of the array are of the integrating type in which a charge is built up on a capacitor which is proportional to the total number of photons which that sensor is exposed to between read-out cycles. The test object gives off a photon flux the magnitude of which is dependent on its absolute temperature. The flux is in the form of discrete photons of light which are of an energy or frequency which depends on the temperature of the body. The flux is not continuous in time but fluctuates randomly about an average value dependent on temperature. The sensors integrate over a period of time which is long relative to the random fluctuations and are thus better able to detect small changes in average temperature which correspond to small changes in average flux.

The infrared sensors of the array are manufactured as part of an overall array which is part of a micro-electronic device. As an inherent property of the array manufacturing process, not all sensors within the array have the same sensitivity or quantum efficiency with respect to measuring the flux which they receive. Conventionally, planar arrays have been adjusted for these individual sensor variations and quantum efficiencies by exposing the array to a uniform flux of infrared radiation and developing a correction for each pixel. These corrections are in the form of a gain and an offset which are stored in a computer memory. When the integrated flux seen by each sensor in the array is periodically read out, it is converted into a digital signal. To form a complete image the digital output of each signal is combined with these offsets to produce an image of the thermal profile of the object imaged on the sensor array. The process of converting the analog signal, which is a measure of the charge accumulated by each sensor during a read-out cycle, employs an analog-to-digital convertor (A/D). The A/D converts the read-out of each sensor into a discrete value with a range dependent upon the number of bits employed by the convertor. A typical 8-bit convertor has 256 possible discrete values--making the smallest resolvable signal approximately 1/256 of the total signal. This severely limits the sensitivity of the detected temperature range.

In conventional I.R. imaging systems it is known to apply a global offset which is equal to the average temperature or signal of the entire array and offset the analog value of each sensor by this global value before it is converted, thereby considerably increasing the precision of the output of the A/D convertor. The present invention achieves much greater precision by applying a local offset to the output of each sensor before it is converted into a digital word. The local offset which corresponds to each sensor will typically be the sensor's average value so that the digital signal which is periodically read from each sensor of the array corresponds to the portion of the signal which is varying in time. With proper synchronization between the cyclical loading of the test object and the frame rate of the infrared array the output of the A/D converted signal will correspond to the stress field induced temperature variations on the test object. A digital lock-in operation may then be performed on the output of each sensor in the array. The result is a test instrument which can form an image of the thermoelastic stresses in an entire test object in the time an instrument employing a slow scan camera using an equivalent sensor, can process a single point in its raster scan. Thus for an array or raster scan 128×128 the total analysis would be 16,384 times as rapid.

It is an object of the present invention to provide an instrument for measuring the stresses in an object which can rapidly produce a scan of the entire object.

It is another object of the present invention to provide a stress measuring instrument employing an array of integrating infrared sensors which precisely monitors small changes in temperature.

It is a further object of the present invention to provide an instrument for detecting stresses in an object which are periodic or quasi-periodic in nature.

It is an additional object of the present invention to provide an instrument for producing a high resolution thermal image of a test object.

It is also an object of the present invention to provide an instrument for determining the stresses within an object where the stresses are elastic and the periodicity is introduced by an external means.

It is yet another object of the present invention to provide an instrument for detecting stresses in an object which employs an array of sensors and digital circuitry which performs a digital signal correlation on each sensor.

Further objects, features, and advantages of the invention will be apparent from the following detailed description when taken in conjunction with the accompanying drawings.

DESCRIPTION OF THE PREFERRED EMBODIMENT

Figure 1:
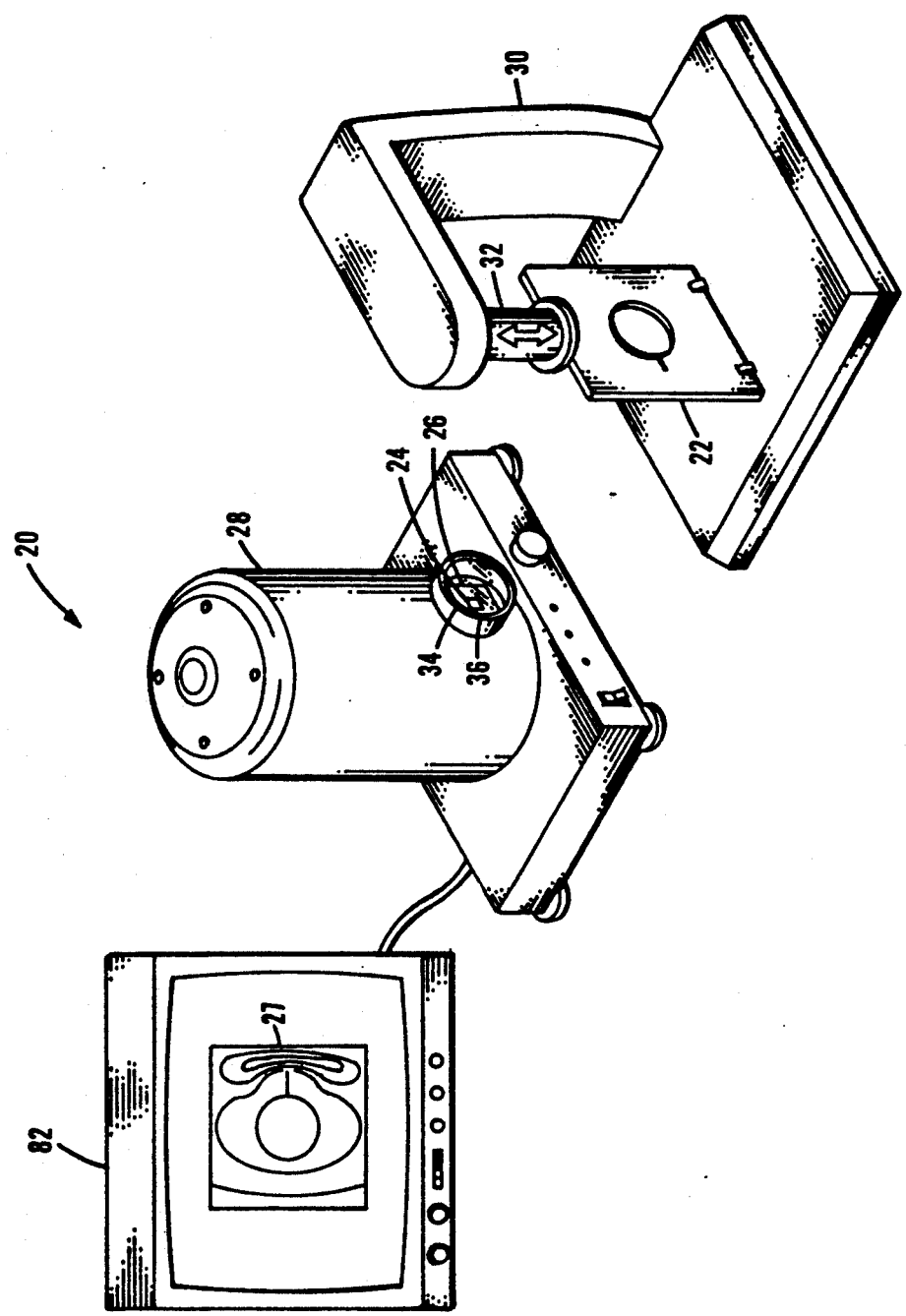
FIG. 1 is an isometric view of the stress distribution measurement instrument of this invention.

Referring more particularly to FIGS. 1-4 wherein like numbers refer to similar parts, an instrument 20 for determining the stresses in an object 22 is shown in FIG. 1. The instrument 20 has a sensor array 24 composed of a multiplicity of flux-integrating sensors. The array is part of an integrated circuit 26. The sensors in the array 24 are sensitive to infrared radiation. In order to reduce thermal noise, the sensor array 24 is placed within a dewar or vacuum bottle 28 which is filled with liquid nitrogen to maintain the dewar at a temperature of approximately 70° K. Other suitable cooling means such as helium, mechanical or thermoelectric coolers may be employed. The instrument 20 will generate numerical data which may be displayed on a video display terminal 82 as a picture 27.

The test object 22 is held in a test fixture 30 where it is subject to cyclical loading by an actuator 32. The cyclical loading causes the various portions of the test object 22 to be subjected to either compression or tension which in turn causes small localized temperature changes in the object 22 which are dependent upon the local stress in the material. The test object 22 is imaged by an infrared optical train 34 which includes an I.R. window 36 in the dewar 28. The window transmits infrared radiation while providing thermal insulation by incorporating a vacuum between elements of the window. The image produced by the optical train 34 is projected onto the sensor array 24 mounted on the integrated circuit 26. The array 24 in an exemplary system employs a high-performance 128×128 InSb focal plane array such as is available from Amber Engineering, Inc., 5756 Thornwood Drive, Santa Barbara, Calif. 93117-3802. In the exemplary 128×128 array, each sensor has a detector which is connected through an indium bump to a high-performance integrating amplifier which converts the detector signal to a band limited voltage.

Figure 2:
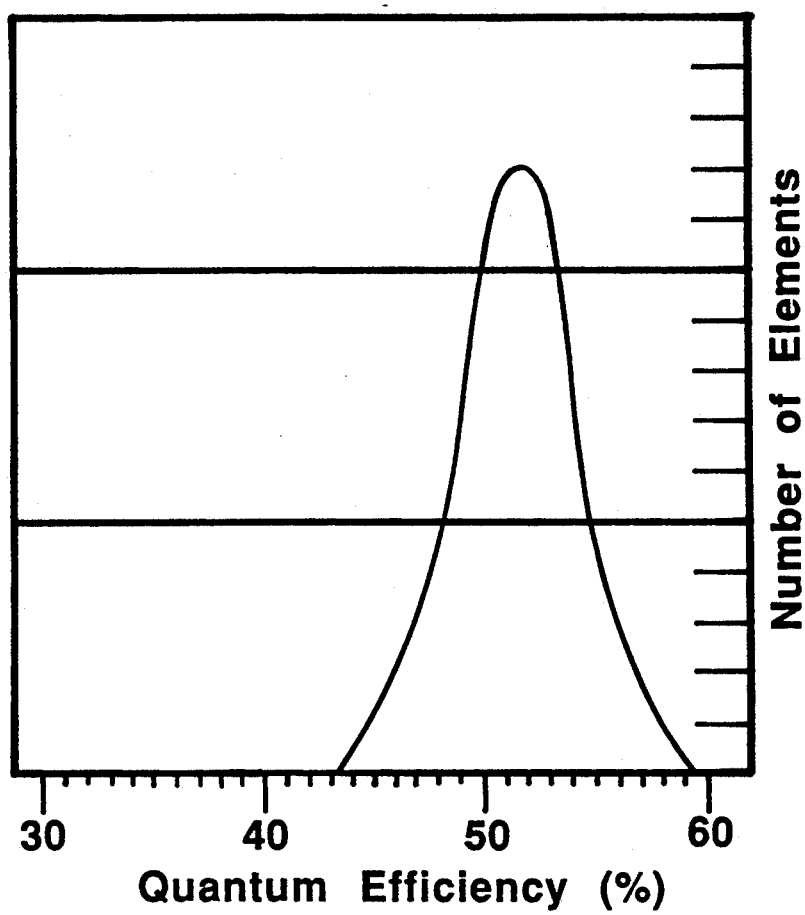
FIG. 2 is a graphical representation of the quantum efficiency distribution of typical sensor elements employed in the sensor array employed in the stress distribution measurement instrument of FIG. 1.
Figure 3:
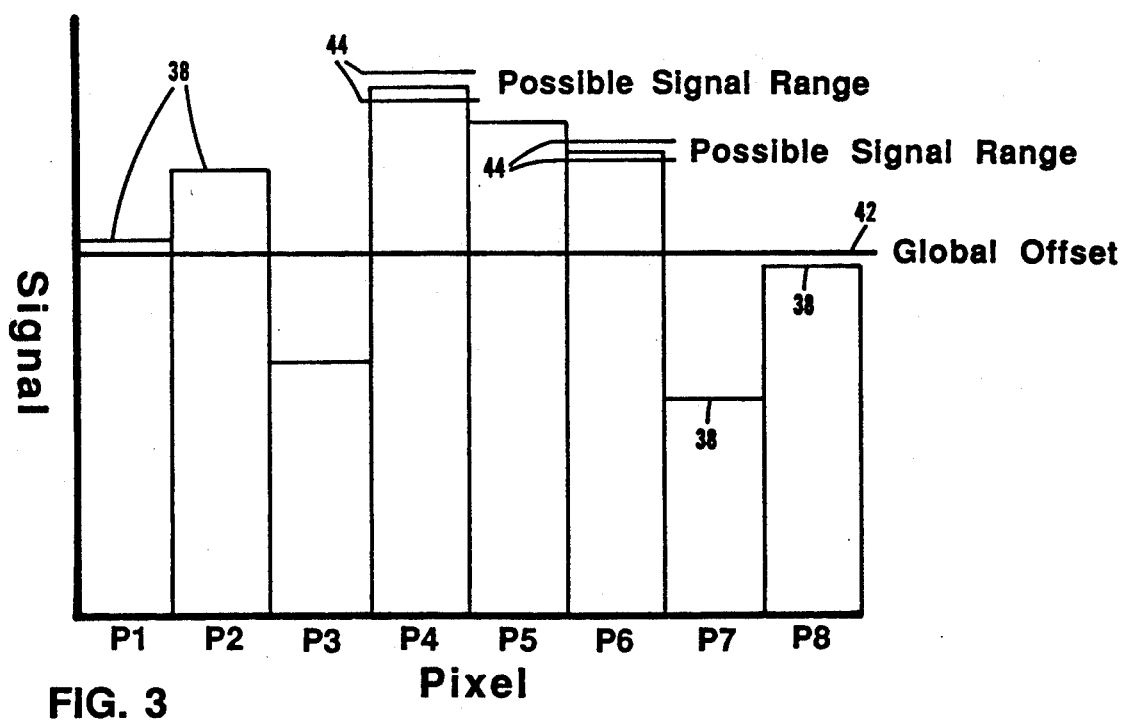
FIG. 3 is a graphical representation of the average signal produced by typical sensor elements of FIG. 2.

The InSb diodes which make-up the sensors of the sensor array 24 have varying quantum efficiency as shown in FIG. 2. Quantum efficiency is the percentage of the infrared photons or infrared flux which is incident upon a particular sensor which that sensor detects. Eight representative sensors or pixels which are all being exposed to approximately equal infrared flux are shown in FIG. 3 and labeled P1-P8. The height of the bars 38 of the graph of FIG. 3 represent the analog signal strength of eight typical sensors in the sensor array 24. Before further processing, the signal strength of each pixel as represented by the bars 38 must be converted to a digital word by means of an analog-to-digital convertor (A/D) 40 shown in FIG. 4.

The analog-to-digital convertor 40 compares the discrete voltages of each pixel, such as those represented in FIG. 3 by P1-P8, to a range of reference voltages and so converts the signal strength into a binary number. Analog-to-digital convertors are available with varying numbers of bits of precision, for example eight. An 8 bit A/D convertor's output is limited to one of two hundred and fifty-six values corresponding to two hundred and fifty-six discrete voltages of equal increments. In order to accurately detect the small fluctuations in the signal from each sensor which is due to the thermoelastic effect, it is desirable to offset the signal from each sensor so that the full range of the A/D convertor corresponds to the signal produced by the thermoelastic effect. This is a much better solution (providing some sort of offset) than improving the accuracy of the A/D by increasing the number of bits and the resolution of the A/D. More bits increase the cost of the A/D convertor and can substantially reduce its speed. Additionally, in some types of A/D convertors, the possibility of a noise-induced error increases with a greater number of bits. It is therefore desirable to use an offset technique which presents the A/D only with the relevant part of the signal from each sensor. One known method is to offset the signal by a global offset which is the average of all the signals of all the sensors in the array 24. The global offset value line 42 is labeled in FIG. 3. However, because of the varying quantum efficiencies of the individual sensors and because there may be a temperature gradient in the test object 22, the signal 38 of individual sensors as shown in FIG. 3 may have values which differ substantially from the global offset value 42. Referring to FIG. 3, sensors P4 and P6 have bracketing lines 44 labeled "possible signal range" which demonstrate the variation in the signal strength 38 which would be expected due to the thermoelastic effect of the stress cycling of the test object 22. To obtain maximum resolution from a given A/D convertor processing signals 38 from the sensors P1-P8 of FIG. 3, the signal 38 from each sensor in the sensor array 24 is offset by an offset voltage which corresponds to the average value of the signal strength 38 for that sensor.

Figure 4:
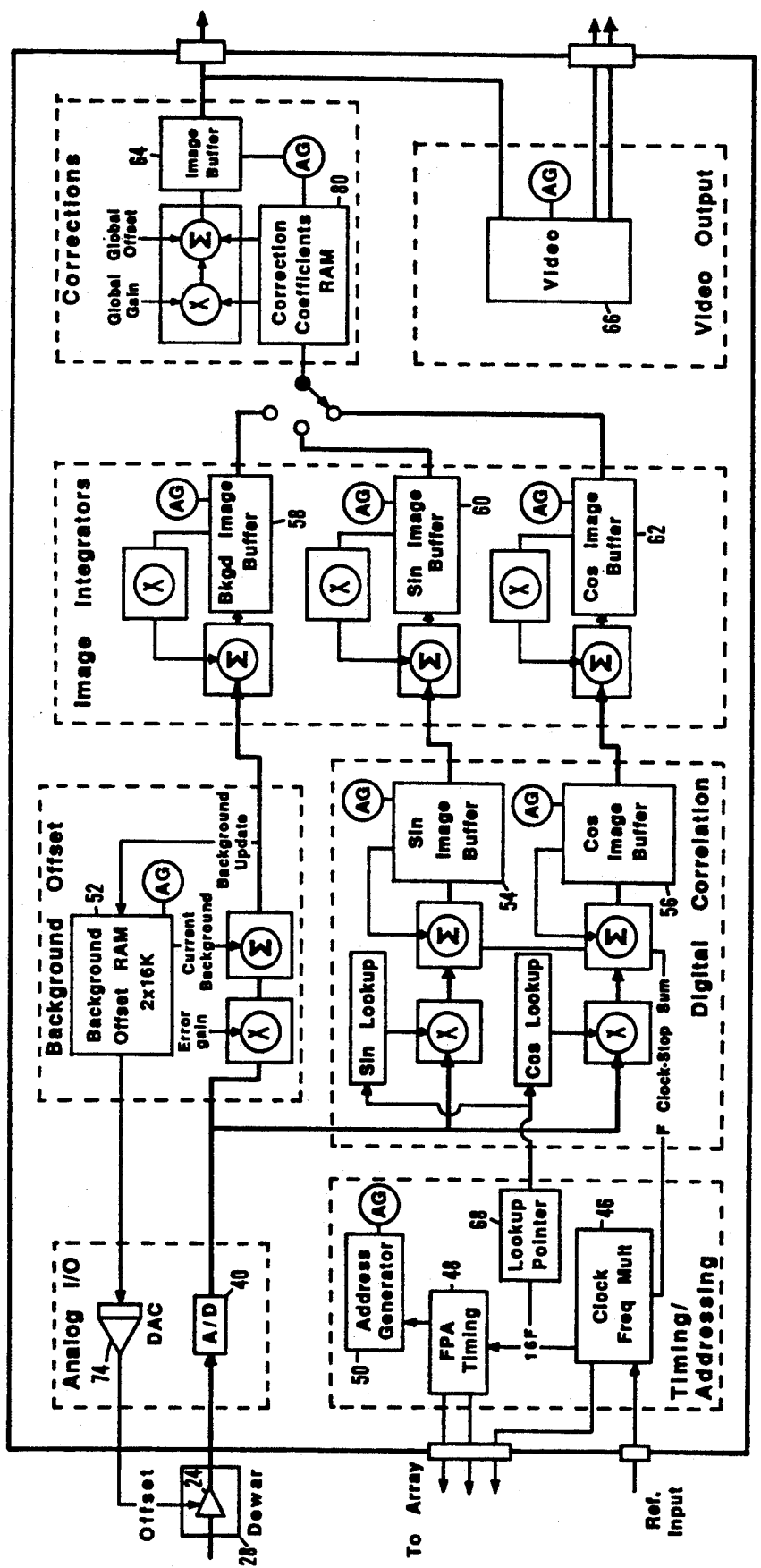
FIG. 4 is a schematic representation of the circuit employed in the stress distribution measurement apparatus of FIG. 1.

FIG. 4 shows a typical block diagram for an exemplary circuit which performs the functions of providing a local offset to the output of each sensor in the array 24 and providing a digital lock-in operation on each sensor in the array 24.

In a typical test setup as shown in FIG. 1, the sample 22 is cyclically loaded by the actuator 32 at a rate of, for example, ten times a second. A reference signal from the actuator 32 is fed to the clock 46 so as to synchronize the readout of the array 24 with the loading cycle produced by the actuator 32. The clock produces a timing signal labeled 16F which is sixteen times the frequency of the loading cycle produced by the actuator 32. This timing signal is used by the focal plane array timing circuit to read out the array 24 sixteen times each loading cycle or one hundred sixty times a second.

The focal plane array timing circuit 48 inputs to an address generator 50 which generates an address which corresponds to each sensor of the array 24 so as each sensor is periodically read its value may be correlated with a unique offset value stored in the offset ram 52.

For a sensor array 24 with 128×128 sensors there are 16,384 unique addresses which correspond to a location in the offset memory 52 and to a location in the image buffers 54, 56, 58, 60, 62, 64, 66 which contains values associated with each individual sensor.

Referring to FIG. 4, the function of the timing/addressing block is to synchronize the signal processing to the loading frequency. The clearest way to assure valid sampling free of aliasing or over-integration is to maintain consistent sampling with respect to the load wave. In the example illustrated in FIG. 4, this is accomplished by using a sixteen times frequency multiplier or sampling. This trigger clocks in sixteen images per load cycle that stay in phase with the load cycle within a small angle error. The trigger also advances the pointer 68 in the sine 70 and cosine 72 look-up tables in the digital correlation block. Even though the load cycling frequency may change, we are assured of 16 samples per load cycle, and the look-up values never change. Since we are doing a sine and cosine correlation, the relative phase of the thermoelastic signal and the load signal can be solved for, and are therefore not critical. In fact, each row of elements in the sensor array 24 will be sampled with a different phase with respect to the frequency. But, these phases are known and are allowed for.

The timing/addressing block also provides an address generator used to drive all image buffers and the correction arrays. It provides a high-speed clock, as well as the X-sinc and Y-sinc signals which cause the progressive read out of the value of each sensor within the array 24. A "timing/addressing" block also passes on a one times frequency clock used by the digital correlation block. In FIG. 4 the background offset block provides the individual sensor offsets which are critical to making best use of the range of the analog-to-digital convertor 40. The background offset block uses a constantly updated integrated value to determine the average value of a particular sensor's output over a stress cycle or 16 frames of data from the array sensor 24. Thus a value is stored in the background offset ram 52 which corresponds to the average signal output by each sensor in the array 24. This average offset value is converted by the digital-to-analog convertor 74 to an offset voltage which is subtracted from each sensor's output by a voltage combiner before it is fed to a scalable amplifier which is used to optimize the A/D conversion dynamic range. Because the background offset RAM 52 contains essentially the average temperature sensed by each sensor in the array 24 this same data can be fed to a background image buffer 58 which may be used to form an image of the average temperature profile of an object such as a conventional steady state camera would produce.

To detect the time-varying signal from the array, a digital correlation or digital lock-in operation is performed by the digital correlation block of FIG. 4. The address generator 50 causes a frame of data, consisting of values for each of the sensors of the sensor array 24, to be read out, offset, and converted from an analog to a digital signal. The values from the sensors are then fed to both the background offset circuit shown in FIG. 4 and to the digital correlation circuit. The values for each frame of data stream simultaneously into the sine lock-in and the cosine lock-in. As the values enter their respective correlation channels, they are multiplied by the appropriate sine or cosine value from the look-up tables. The 16-times clock pushes the pointer to the value that corresponds to the image position. Directed by the address generator of the timing/address block, values are summed with the previous sample values of the current correlation set. After the completion of the 16-sample set, the F-clock sends correlation set sums to the image integrators and zeros the correlation buffers 54, 56.

The monocycle digitally locked-in image then goes to the image integrators whose function is to set the camera reactance. The time constant is a multiplier less than unity that sets the time average weighting. It has the same effect as the time constant on a lock-in amplifier and can set the noise bandwidth similarly.

Finally, the output of the image integrators is sent to a correction circuit where a two point gain and global offset corrections are applied from a correction RAM 80. The output of the correction circuit may be output to a computer for further processing or directly to a video output circuit 66 which displays on a monitor 82, as shown in FIG. 1, either the average value of the temperature profile on the test object 22 or the time varying component which correlates with the stress distribution in the object. The apparatus of FIG. 1 employing the circuitry shown in FIG. 4, functions as follows:

A sensor array 24 shown in FIG. 1 and schematically in FIG. 4 consists of 128×128 for a total of 16,384 photo diode sensors. Each photo diode is connected to a capacitor and as photons impact the surface of the photo diode, the capacitor is charged. Because the capacitor continues to charge as long as the photo diode receives photons, the capacitor acts as an integrator which integrates the output of the diode over the read out cycle of the array 24. Periodically, for example 160 times a second, the values on the capacitors are sequentially read out. In order to maximize the resolution of the photo diode sensor array a local offset is used with each sensor. Before the voltage represented by the charge on each diode's capacitor is converted to a digital signal, the analog voltage read out from each capacitor is offset by a voltage. This offset voltage is obtained by converting into an analog voltage a stored digital offset which corresponds to a particular photo diode sensor. This analog voltage is then subtracted from the output of a particular sensor in the array. This output signal is then sent to a scalable amplifier to optimize the A/D conversion dynamic range and the digital value of the time varying portion of each photo diode's signal over each integration period and is then read out for further processing. Part of the processing is to use the value of the time-varying signal over an entire load cycle of the test object, in our example 16 frames of data, to update the average value which is used to offset each sensor. If the output of the sensor array 24 is thought of as a picture, one complete set of data may be thought of as a frame with the output of each sensor comprising a single pixel (the smallest element of a picture). Because the sample is being driven by a sinusoidal ten Hz load cycle the thermoelastic signal detected by the photo diode sensor array 24 will be correlated with this 10 Hz signal. Therefore any one of a number of signal processing routines may be used to improve the signal-to-noise ratio of the signal. For instance, by performing a Fourier transform on the time domain value of a single pixel and so moving into the frequency domain, it is apparent that the signal of interest will correspond to 10 Hz and its harmonics. And therefore the strength of the 10 Hz signal will represent the thermoelastic effect. The narrow band width of the correlated signal will easily be distinguished from noise which is evenly distributed over frequency.

If the dynamic loading of the test object is at least quasi-periodic, even if the drive frequency is unknown, analysis of the output of a pixel or the entire frame of data in the frequency domain will show the thermoelastic signal in terms of a narrow band of high amplitude. Where it is desirable to perform nondestructive tests on a steel bridge, for example, it would be possible to image the bridge while it is being excited by vehicles being driven over it so that it oscillates at its characteristic frequency. The characteristic frequency oscillations would cause time-varying stresses within the bridge which could be extracted from the integrated outputs of the array sensor over time by performing a correlation analysis such as a Fourier transform which would determine the thermal emissions which occurred in narrow frequency bands. These frequencies can reasonably be assumed to be the natural frequencies of the bridge or in many cases the natural frequencies of the bridge will be known. It should be noted that after the amplitude of the thermoelastic signal for a Particular pixel/sensor is determined that amplitude must still be adjusted by a gain which corresponds to the relative quantum efficiency of a particular pixel/sensor so that the amplitude of a particular pixel/sensor corresponds directly to the magnitude of the time-varying signal and therefore show the stress at a particular point in the imaged object.

For the purposes of the following discussion, "A" is a least-squares coefficient; "B" is also a least-squares coefficient; "Y" is the continuous time function of sampled data; "$Y_n$" is the discrete time function of sampled data; "yn" is the discrete time function of reference wave; $\beta(n)$ is a parameter; $\Gamma$ is the period of arbitrary discrete function; and $\Delta^2$ is the least squares variance.

An approach to analyzing signals which are not sinusoidal may be illustrated by considering an arbitrary dynamic function modeled by the formula $$Y = A + B\, F(t)$$

We can make this discrete by $$Y_n = A + BF\left(\frac{\Gamma}{N}\left(n - \frac{1}{2}\right)\right)$$

where gamma is the period of the function. Again, we want to minimize the square deviation, $$\Delta^2 = \sum_{n=1}^{N} (y_n - Y_n)^2$$

where $$\frac{\partial \Delta^2}{\partial A} = \frac{\partial}{\partial A} \sum_{n=1}^{N} \left(y_n - A - BF\left(\frac{\Gamma}{N}\left(n - \frac{1}{2}\right)\right)\right)^2 = 0$$

$$\frac{\partial \Delta^2}{\partial B} = \frac{\partial}{\partial B} \sum_{n=1}^{N} \left(y_n - A - BF\left(\frac{\Gamma}{N}\left(n - \frac{1}{2}\right)\right)\right)^2 = 0$$

where

-continued $$\beta(n) = \frac{\Gamma}{N}\left(n - \frac{1}{2}\right)$$

This results in two equations with two unknowns, $$\frac{\partial \Delta^2}{\partial A} = -2 \sum_{n=1}^{N} (y_n - A - BF(\beta(n))) = 0$$

$$\frac{\partial \Delta^2}{\partial B} = -2 \sum_{n=1}^{N} [(y_n - A - BF(\beta(n)))F(\beta(n))] = 0$$

Simplifying, $$A \sum_{n=1}^{N} + B \sum_{n=1}^{N} F(\beta(n)) = \sum_{n=1}^{N} y_n$$

$$A \sum_{n=1}^{N} F(\beta(n)) + B \sum_{n=1}^{N} F^2(\beta(n)) = \sum_{n=1}^{N} y_n F(\beta(n))$$

Putting these into matrix notation, $$\begin{bmatrix} N & \sum_{n=1}^{N} F(\beta(n)) \\ \sum_{n=1}^{N} F(\beta(n)) & \sum_{n=1}^{N} F^2(\beta(n)) \end{bmatrix} \begin{bmatrix} A \\ B \end{bmatrix} = \begin{bmatrix} \sum_{n=1}^{N} y_n \\ \sum_{n=1}^{N} y_n F(\beta(n)) \end{bmatrix}$$

and forcing the off-diagonal terms to fall out by adding an offset to the sampled reference $$\begin{bmatrix} N & 0 \\ 0 & \sum_{n=1}^{N} F^2(\beta(n)) \end{bmatrix} \begin{bmatrix} A \\ B \end{bmatrix} = \begin{bmatrix} \sum_{n=1}^{N} y_n \\ \sum_{n=1}^{N} y_n F(\beta(n)) \end{bmatrix}$$

For the non-diagonalized case $$A = \frac{\sum_{n=1}^{N} y_n \sum_{n=1}^{N} F^2(\beta(n)) - \sum_{n=1}^{N} F(\beta(n)) \sum_{n=1}^{N} y_n F(\beta(n))}{N \sum_{n=1}^{N} F^2(\beta(n)) - \left[\sum_{n=1}^{N} F(\beta(n))\right]^2}$$

$$B = \frac{N \sum_{n=1}^{N} y_n F(\beta(n)) - \sum_{n=1}^{N} y_n \sum_{n=1}^{N} F(\beta(n))}{N \sum_{n=1}^{N} F^2(\beta(n)) - \left[\sum_{n=1}^{N} F(\beta(n))\right]^2}$$

For the diagonalized case, $$A = \frac{1}{N} \sum_{n=1}^{N} y_n$$

$$B = \frac{\sum_{n=1}^{N} y_n F(\beta(n))}{\sum_{n=1}^{N} F^2(\beta(n))}$$

This suggests that some complex dynamic-function work could be performed by the fast and simple digital electronics that will be used for the standard thermal stress analysis measurements.

It should be noted that although the thermoelastic stress analysis instrument has been described as utilizing InSb detectors which have a spectral response from 1 to 5.5 micrometers, sensors of broader band sensitivity would of course be advantageously employed. HgCdTe sensor arrays which have a broader band sensitivity, of 1 to 10 micrometers, may alternatively be employed. It should also be understood that the stress measurement instrument shown in FIG. 1 is not limited to a particular type of sensor array but applies to any array of sensors capable of integrating infrared over a read out cycle. The typical sensor array is a multiplexed device.

Because the thermoelastic measurement instrument 20 uses a multitude of sensors simultaneously imaging the test object and because each sensor is digitally correlated or signal processed in parallel, although the values are read out from the array 24 sequentially, the stress measurement unit of FIG. 1 will be able to form a correlated image of the stress field of an object 22 in approximately the time that a slow scan sensor employing a raster scanning system and a single sensor could integrate a single point on the object 22. Therefore, where a 16,384 sensor array is utilized, a correlated image of the stresses in an object may be performed in 1/16,384 the time assuming array sensors of bandwidth and efficiency similar to those of the slow scan sensor. Because the sensors of the stress measurement instrument 20 integrate over essentially all the time between readout cycles, the signal-to-noise ratio of the individual sensor outputs is relatively high before digital correlation starts and therefore the stress measurement instrument 20 will have comparable speed advantages over a video fast scan system.

It is understood that the invention is not confined to the particular construction and arrangement of parts herein illustrated and described, but embraces such modified forms thereof as come within the scope of the following claims.

I claim:

1. An apparatus for measuring the stress distribution in an object comprising:
   a) an infrared detecting array having a plurality of infrared sensors wherein the array is adapted to receive an infrared image corresponding to an object, and wherein each detector has a capacitor adapted to charge in response to the photon flux incident upon said sensor;
   c) a read out circuit adapted to periodically measure the charge on each capacitor;
   d) a memory adapted to store a local off-set value for each sensor within the array;
   e) a digital-to-analog convertor adapted to produce an analog voltage proportional to a local off-set value corresponding to a particular array sensor read from the memory; and
   f) an analog-to-digital convertor operably connected to the read out circuit and the digital-to-analog convertor to provide a digital signal proportional to the differential of the charge on each sensor capacitor and its corresponding analog local off-set value.

2. The apparatus of claim 1 wherein the memory stores off-set values for each infrared sensor in the array which are proportional to the quantum efficiency of each sensor.

3. The apparatus of claim 1 wherein the memory stores an off-set value for each sensor in the array which corresponds to that sensor's time-averaged value.

4. The apparatus of claim 1 wherein the infrared sensors are indium antimonide photo diodes.

5. The apparatus of claim 1 wherein the infrared sensors are photo diodes employing mercury-cadmium-telluride.

6. The apparatus of claim 1 further comprising an object undergoing time-varying stress and an infrared optical imaging system which projects an image of the object on the infrared radiation-detecting array.

7. The apparatus of claim 6 further comprising an actuator adapted to induce periodic stress in the object at a predetermined frequency.

8. The apparatus of claim 7 wherein an object is undergoing periodic loading, and further comprising a digital correlator which correlates the output of the infrared radiation detector array as supplied by the analog-to-digital convertor with the periodicity of the load to improve the signal-to-noise ratio of the infrared radiation which corresponds to the periodically induced stress.

9. An apparatus for detecting time-variant thermal radiation of an object, comprising:
   a) an array having a plurality of flux-integrating sensors adapted to integrate the flux from discrete areas of an object;
   b) a first circuit which produces a first timing signal with a period approximately equal to the period of the time-variant thermal radiation;
   c) a second circuit which produces a second timing signal having a frequency greater than the frequency of the first timing signal, wherein the flux integrating sensor integrates over a time corresponding to the period of the second timing signal; and
   d) an output circuit which outputs the value of the flux-integrating sensors adjusted by a signal which is proportional to the average value of the sensor integrated over a time corresponding to the first timing signal period or multiple of the first timing signal period so that the output signal corresponding to the time variant thermal radiation has an increased resolved signal resolution.

10. The apparatus of claim 9 further comprising:
    a) a digital local off-set memory having an address corresponding to each sensor in the array;
    b) a digital-to-analog convertor adapted to convert the stored value in the offset memory to a local offset voltage for a particular sensor;
    c) a voltage combiner which combines the local offset voltage with the output voltage of the particular sensor so that the output voltage is offset by the local offset voltage; and
    d) an analog-to-digital convertor connected to the voltage combiner and adapted to output a digital word proportional to the time-varying portion of the sensor signal.

11. The apparatus of claim 10 further comprising a scalable amplifier amplifying the output of the voltage combiner before the voltage is supplied to the digital convertor so making full use of the range of the analog-to-digital convertor.

12. The apparatus of claim 9 further comprising a driver for causing periodic stress in the object at approximately the predetermined frequency.

13. The apparatus of claim 9 further comprising an object undergoing time-varying stress and an infrared optical imaging system which projects an image of the object on the array of flux-integrating sensors.

14. The apparatus of claim 9 further comprising a digital correlator which correlates the output of each sensor in the array as supplied by the analog-to-digital convertor with the periodicity of the load to improve the signal-to-noise ratio of the time-varying thermal radiation which corresponds to the periodically induced stress.

15. The apparatus of claim 9 wherein the array of flux integrating sensors is a multiplexed device employing indium antimonide photo diodes.

16. The apparatus of claim 9 wherein the array of flux integrating sensors is comprised of photo diodes employing mercury-cadmium-telluride.

17. A stress distribution measuring instrument comprising:
    a) an infrared detecting array containing a multiplicity of infrared sensors arrayed on a surface and adapted for receiving an infrared image corresponding to an object undergoing cyclical loading in which it is desired to measure the stress distributions, wherein each sensor has a capacitor adapted to charge in response to a photon flux incident upon the detector;
    b) a means for periodically measuring the charge on each capacitor; and
    c) a multiplicity of digital correlators adapted to perform correlation on the periodically read out data from each of the multiplicity of sensors.

18. The apparatus of claim 17 further comprising: a memory adapted to contain an offset value for each detector within the array; a digital-to-analog convertor for producing an analog signal proportional to an offset value corresponding to a particular sensor in the memory; a voltage combiner for supplying the offset voltage to the measured charge on each capacitance means; and an analog-to-digital convertor connected to the combiner to output a digital word corresponding to the value of each sensor offset by the offset value stored in the memory.

19. The apparatus of claim 17 wherein the digital correlator further comprises a sensor mounted on the object undergoing cyclical loading which provides a reference signal corresponding to the period and phase of the periodic stress in the object which is used by the digital correlators to improve the signal-to-noise ratio of the time-varying component of the sensor outputs.

20. The apparatus of claim 17 wherein the infrared sensors employ indium antimonide photo diodes.

21. The apparatus of claim 17 wherein the infrared sensors are comprised of photo diodes employing mercury-cadmium-telluride.

22. A process for determining the stress in an object undergoing cyclical loading comprising the steps of:
    a) projecting the emitted infrared radiation of an object undergoing cyclical loading onto an infrared detecting planar array having a plurality of integrating sensors;
    b) periodically reading out the integrated voltage of each sensor in the array;
    c) combining the voltage of each sensor with a local offset voltage which corresponds to each sensor; and
    d) converting the combined voltage to a digital signal wherein the digital output has improved precision.

23. The process of claim 22 wherein the combined voltage is amplified by a scalable amplifier before it is converted to a digital signal to optimize the dynamic range of the conversion of the analog voltage to a digital value.

24. The process of claim 22 wherein the local offset voltage is obtained by reading out from a digital memory a value which corresponds to each sensor, and converting the digital value to an analog voltage.

25. The process of claim 22 further comprising the steps of performing a digital lock-in on the digital output of each sensor in the array over time so improving the signal-to-noise ratio of the detected infrared radiation which corresponds to the stress in the object.

26. The process of claim 25 further comprising the steps of imaging the stress in an object by displaying the correlated signal of the sensors in the array as a video image wherein the varying amplitude of the correlated signal of each sensor is indicated by a differing color or intensity in the image, the imaging of the sensor outputs being arrayed so as to correspond to the infrared image projected onto the sensor array.

27. A method for determining the stress distribution on an object utilizing the thermoelastic effect, comprising;

a) subjecting the object to a cyclical load so as to stimulate thermoelastic infrared emissions;
b) receiving the infrared emissions from the object on an infrared sensor array comprised of a plurality of sensors;
c) reading out a voltage from each sensor corresponding to the infrared emissions incident on that sensor;
d) recalling a stored local offset value from a digital memory corresponding to each sensor and converting the digital value to an analog voltage;
e) combining the sensor voltage and the corresponding local offset voltage for each sensor;
f) converting the combined analog voltage to a digital value.

28. The method of claim 27 wherein the local offset value for each sensor corresponds to the average voltage read out from that sensor over a plurality of load cycles.

29. The method of claim 27 further comprising displaying the processed digital values for each sensor as a visible image on a video display.

* * * * *